(12) United States Patent
Khatam et al.

(10) Patent No.: US 10,856,743 B2
(45) Date of Patent: Dec. 8, 2020

(54) METHODS AND APPARATUSES FOR MEASURING MULTIPLE VITAL SIGNS BASED ON ARTERIAL PRESSURE WAVEFORMS

(71) Applicant: OSLERMD, INC., San Diego, CA (US)

(72) Inventors: Bahman Khatam, Escondido, CA (US); John Richard Gelm, Coronado, CA (US)

(73) Assignee: OslerMD, Inc., San Diego, CA (US)

( * ) Notice: Subject to any disclaimer, the term of this patent is extended or adjusted under 35 U.S.C. 154(b) by 666 days.

(21) Appl. No.: 15/249,257

(22) Filed: Aug. 26, 2016

(65) Prior Publication Data
US 2017/0055846 A1   Mar. 2, 2017

Related U.S. Application Data

(60) Provisional application No. 62/258,694, filed on Nov. 23, 2015, provisional application No. 62/211,604, filed on Aug. 28, 2015.

(51) Int. Cl.
*A61B 5/0205*   (2006.01)
*A61B 5/02*      (2006.01)
(Continued)

(52) U.S. Cl.
CPC ........ *A61B 5/0205* (2013.01); *A61B 5/02028* (2013.01); *A61B 5/02108* (2013.01);
(Continued)

(58) Field of Classification Search
None
See application file for complete search history.

(56) References Cited

U.S. PATENT DOCUMENTS 5,140,990 A * 8/1992 Jones ............... A61B 5/021
                                                    600/480
2002/0026114 A1* 2/2002 Nissila ............. A61B 5/02438
                                                    600/384

(Continued)

OTHER PUBLICATIONS

Middleton, et al., Spectral analysis of finger photoplethysmographic waveform variability in a model of mild to moderate haemorrhage, Journal of Clinical Monitoring and Computing, Oct. 11, 2008, pp. 343-353, vol. 22, No. 5.

(Continued)

*Primary Examiner* — Etsub D Berhanu
(74) *Attorney, Agent, or Firm* — Mintz Levin Cohn Ferris Glovsky and Popeo, P.C.

(57) ABSTRACT

Vital sign sensor apparatuses which measures vital signs based on arterial pressure waveforms are described. In some embodiments, the apparatus includes an infrared sensor configured to capture at least a portion of an arterial pulse pressure waveform from a user. The apparatus further includes a processor configured to determine a maximum point for each of a plurality of peaks of the arterial pulse pressure waveform, and a corresponding first timestamp. The processor also determines one or more vital signs (e.g., a heart rate for a user, a heart rate variation of the user, a respiration rate of the user, and/or an arterial pulse pressure of the user) based at least in part on the plurality of maximum points and the plurality of corresponding timestamps. Related systems, methods, and articles of manufacture are also described.

19 Claims, 13 Drawing Sheets

(51) Int. Cl.
    *A61B 5/00*     (2006.01)
    *A61B 5/021*    (2006.01)
    *A61B 5/024*    (2006.01)
    *A61B 5/08*     (2006.01)
    *A61B 5/1455*   (2006.01)
    *A61B 5/0245*   (2006.01)
    *A61B 5/0402*   (2006.01)

(52) U.S. Cl.
    CPC .......... *A61B 5/6826* (2013.01); *A61B 5/7278* (2013.01); *A61B 5/7282* (2013.01); *A61B 5/0245* (2013.01); *A61B 5/02405* (2013.01); *A61B 5/02416* (2013.01); *A61B 5/02433* (2013.01); *A61B 5/0402* (2013.01); *A61B 5/0816* (2013.01); *A61B 5/14551* (2013.01); *A61B 5/14552* (2013.01)

(56)         References Cited

U.S. PATENT DOCUMENTS

| | | | | |
|---|---|---|---|---|
| 2002/0188214 | A1* | 12/2002 | Misczynski | A61B 5/0006 600/516 |
| 2003/0163054 | A1* | 8/2003 | Dekker | A61B 5/02416 600/502 |
| 2006/0189872 | A1* | 8/2006 | Arnold | A61B 5/0205 600/483 |
| 2008/0045847 | A1 | 2/2008 | Farag et al. | |
| 2008/0157980 | A1* | 7/2008 | Sachanandani | A61B 5/0031 340/573.1 |
| 2008/0161707 | A1* | 7/2008 | Farringdon | A61B 5/0428 600/509 |
| 2009/0099426 | A1* | 4/2009 | Sachanandani | A61B 5/042 600/301 |
| 2010/0268093 | A1* | 10/2010 | Balji | A61B 5/0205 600/484 |
| 2010/0298656 | A1* | 11/2010 | McCombie | G16H 50/50 600/301 |
| 2014/0066782 | A1* | 3/2014 | Addison | A61B 5/0456 600/476 |
| 2014/0303454 | A1* | 10/2014 | Clifton | A61B 5/0205 600/301 |
| 2015/0164361 | A1* | 6/2015 | Lunner | H04R 25/02 600/379 |
| 2015/0342466 | A1* | 12/2015 | Thakur | A61N 1/3624 600/484 |

OTHER PUBLICATIONS

Pinheiro, et al., Heart rate variability virtual sensor application in blood pressure assessment system, Proceedings of the Sixth lasted International Conference on Biomedical Engineering, Feb. 13-15, 2008, pp. 79-82.

* cited by examiner

METHODS AND APPARATUSES FOR MEASURING MULTIPLE VITAL SIGNS BASED ON ARTERIAL PRESSURE WAVEFORMS

CROSS REFERENCE TO RELATED APPLICATIONS

This application claims the benefit of U.S. Provisional Application No. 62/211,604 filed Aug. 28, 2015 and entitled APPARATUS USING AN INFRARED SENSOR TO ACQUIRE, PROCESS, ANALYZE, AND EXTRACT CARDIOVASCULAR AND PULMONARY BIOMETRICS FROM AN ARTERIAL PRESSURE WAVEFORM and U.S. Provisional Application No. 62/258,694 filed Nov. 23, 2015 and entitled INTEGRATING MULTIPLE MEDICAL VITAL SIGNS SENSORS INTO A WIRELESS HEALTH AND MEDICAL APPARATUS PLATFORM IN CONJUNCTION WITH MEDICAL DEVICES, SMART APPLICATION, CLOUD STORAGE, AND BACKEND DATABASE, the disclosures of which are incorporated herein by reference.

FIELD

The subject matter disclosed herein relates to wireless medical sensors for monitoring a user's health and/or vital signs and/or infrared monitoring of cardiovascular and pulmonary biometrics from arterial pressure waveforms.

BACKGROUND

With the rapid growth in the field of mobile health and telemedicine there is an increasing demand for more integrated, less fragmented, with little, or no, calibration required, as well as non-invasive ways to collect patients' health and medical vital signs from the onboard sensors quickly such as in less than 30 seconds after the valid detection of signals in various settings or use environment.

Extracting and monitoring medical signs from hemodynamic waveforms can provide insight to the quality of heart functioning and the detection of current and impending cardiac and pulmonary conditions. Early detection can enable a quicker realization of an unhealthy heart condition thus triggering early intervention and preventative strategies

SUMMARY

Vital sign sensor apparatuses which measures vital signs based on arterial pressure waveforms are described. In some embodiments, the apparatus includes an infrared sensor configured to capture at least a portion of an arterial pulse pressure waveform from a user. The apparatus further includes a processor configured to determine, for each of a plurality of peaks of the arterial pulse pressure waveform, a maximum point. The processor is further configured to determine, for each of the maximum points, a corresponding first timestamp. The processor is further configured to determine one or more vital signs based at least in part on the plurality of maximum points and the plurality of corresponding timestamps. In various embodiments, the one or more vital signs includes at least one of a heart rate for a user, a heart rate variation of the user, a respiration rate of the user, and an arterial pulse pressure of the user.

In some embodiments, the above-noted aspects may further include features described herein, including one or more of the following: determining the heart rate by generating a plurality of peak rates by subtracting, for each of the plurality of peaks, the corresponding first timestamp of a most recent peak from the corresponding first timestamp of the current peak; determining the heart rate by averaging the plurality of peak rates; determining the heart rate by determining a maximum rate from the plurality of peak rates, determining a minimum rate from the plurality of peak rates, and/or determining a standard deviation from the plurality of peak rates; determining the respiration rate by determining a fundamental frequency of the arterial pulse pressure waveform. In some embodiments, determining the maximum point includes determining, for a plurality of subsequent samples of the arterial pulse pressure waveform, whether a current sample is greater in pressure than a prior sample, storing the current sample when the current sample is greater in pressure than the prior sample, determining whether a threshold number of subsequent samples are not greater than the maximum point, and setting the stored sample as the maximum point when the threshold number of subsequent samples are not greater than the maximum point.

In various embodiments, the processor can be further configured to determine, for each of a plurality of troughs of the arterial pulse pressure waveform, a minimum point, determine, for each of the minimum points, a corresponding second timestamp, and/or determine the one or more vital signs based at least in part the plurality of minimum points and the plurality of corresponding second timestamps. In certain embodiments, the infrared sensor is configured to capture the at least the portion of the arterial pulse pressure waveform from the user's finger via providing signals from a light emitting diode and measuring reflections via a phototransistor. Additionally or alternatively, the apparatus further includes a peripheral capillary oxygen saturation sensor configured to measure oxygen saturation from a user's second finger, and one or more electrocardiography sensors configured to measure an electrocardiography waveform from a user's third finger, wherein the one or more electrocardiography sensors are further configured to measure one or both of the respiration rate and the heart rate from a user's fourth finger.

The above-noted aspects and features may be implemented in systems, apparatuses, methods, and/or computer-readable media depending on the desired configuration. The details of one or more variations of the subject matter described herein are set forth in the accompanying drawings and the description below. Features and advantages of the subject matter described herein will be apparent from the description and drawings, and from the claims. In some example embodiments, one of more variations may be made as well as described in the detailed description below and/or as described in the following features.

Where practical, like labels are used to refer to the same or similar items in the figures.

DETAILED DESCRIPTION

Figure 1:
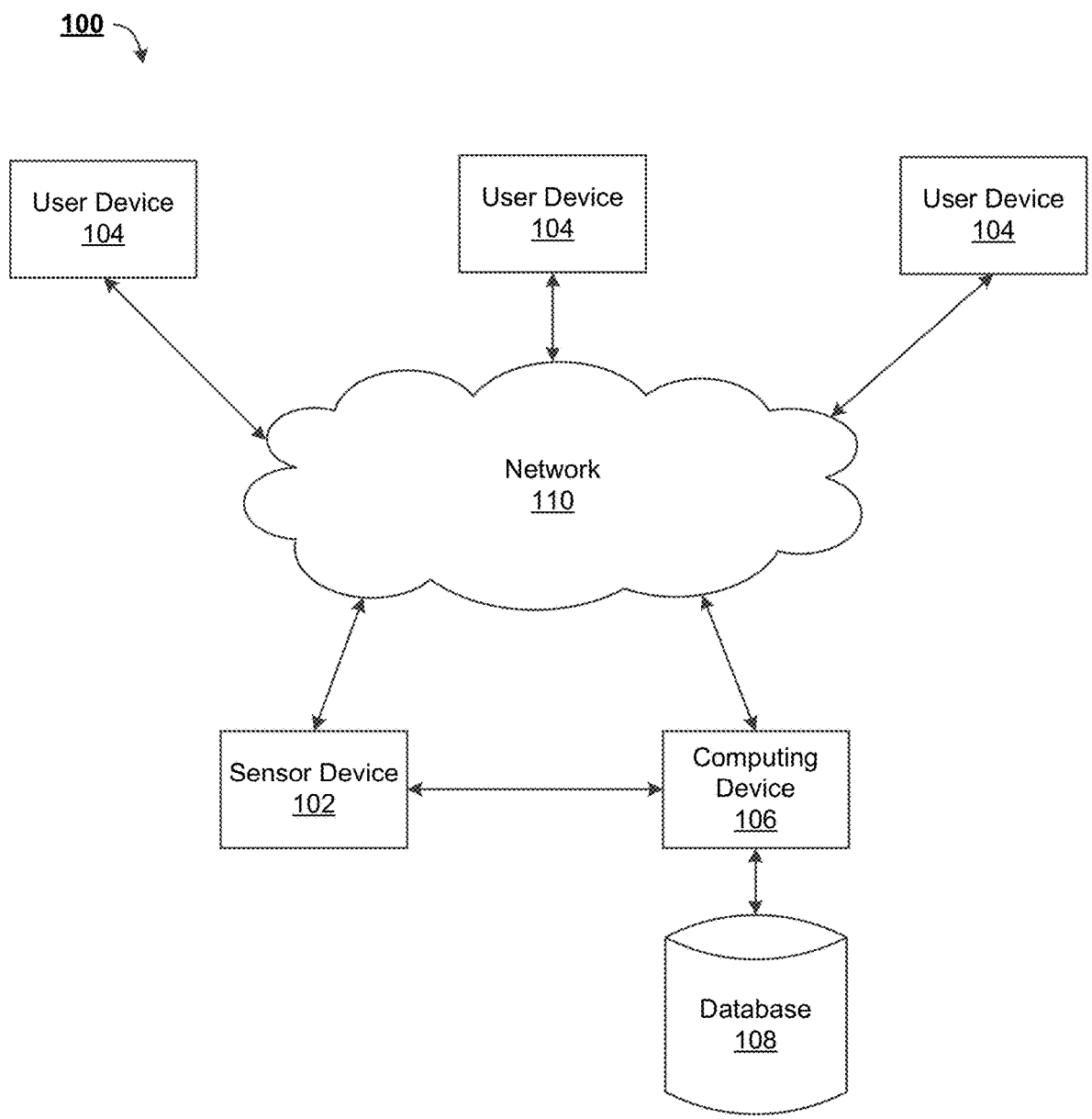
FIG. 1 illustrates an example of a system in which a sensor device for determining vital signs may be implemented, in accordance with some example embodiments.

FIG. 1 illustrates an example system 100 in which a sensor device 102 for determining vital signs may be implemented, in accordance with some example embodiments. In some aspects, the sensor device 102 may be an electronic device capable of measuring a person's (referred to herein as a "user") vital signs through the use of one or more sensors. The vital signs may include traditional vital signs and/or additional health signs. For example, the vital signs tested/determined can be one or more of body temperature, weight, oxygen saturation, glucose level, pulse/heart rate, heart rate fluctuation, respiration rate, blood pressure, pulse pressure, and/or the like. Similarly, certain waveforms may be detected/measured in order to aid in the determination of vital signs measurements, such as an arterial pressure waveform and/or a cardio audio waveform. The sensors may be one or more of resistive sensor(s), surface acoustic sensor(s), capacitive sensor(s), infrared sensor(s), electrocardiography (ECG) sensor(s), peripheral capillary oxygen saturation (SpO2) sensor(s), optical sensor(s), pressure sensor(s), ultrasonic sensor(s), humidity sensor(s), gas sensor(s), motion sensor(s), acceleration sensor(s), displacement sensor(s), force measurement sensor(s), and/or color sensor(s).

Before, during, and/or after measuring a user's vital signs, the sensor device 102 may communicate with a computing device 106. In some aspects, the sensor device 102 may connect with the computing device 106 via one or more of Bluetooth (e.g., low energy) communications, Near-field communications (NFC), ZigBee communications, a universal serial bus (USB), wireless USB, device-to-device communications, and/or the like. As illustrated, the computing device 106 may be in communication with a database 108, which may be used to store vital sign information, user data, and/or the like. In some embodiments, the computing device 106 may be used to initialize measurement of the user's vital signs (e.g., by accepting information about the user), and/or may be used to display resulting measurements of the user's vital signs. For example, a user may place their hand(s) on the sensor device and may see one or more visualizations of their vital signs in real time and/or after their vital signs have been properly scanned.

Although the sensor device 102 and the computing device 106 are illustrated as separate, in some embodiments, the computing device 106 may be part of the sensor device 102, and therefore the sensor device 102 may access and/or provide information to the database 108.

As further illustrated, the sensor device 102 and/or the computing device 106 may communicate over a network 110 (e.g., with each other and/or with others). In various aspects, the network 110 can include one or more of a local area network (LAN), a wireless LAN (WLAN), a personal area network (PAN), a wide area network (WAN), a cellular network, the internet, and/or the like. As further illustrated, one or more user device 104 may also utilize the network 110, and may therefore be in communication with the sensor device 102 and/or the computing device 106. User devices 104 may be computing devices which are capable of controlling, accessing, and/or communicating with other computing device. For example, in some aspects, a user device 104 may be used to provide information to and/or receive information from the sensor device 102, such as updates, maintenance information, user data, test results, and/or the like.

In some aspects, the computing device 106 may provide backend services/software for the sensor device 102. For example, in various embodiments, the sensor device 102 and/or the computing device 106 may utilize cloud-based storage (e.g., via database 108 or physical and/or virtual storage located elsewhere). In some embodiments, the computing device 106 may be a phone, tablet, personal computer, or other device. In accordance with these embodiments, the computing device may operate according to an iOS, Android, Mac, Windows, Linux, or other operating system. The computing device 106 may access one or more cloud-computing services that are running on a secure HIPPA-compliant server (e.g., over the internet).

In some aspects, one or more of the sensor device 102, the user device(s) 104, the computing device, and/or the database 108 may be used by a healthcare professional, and therefore these persons may also be referred to as users.

Figure 2A:
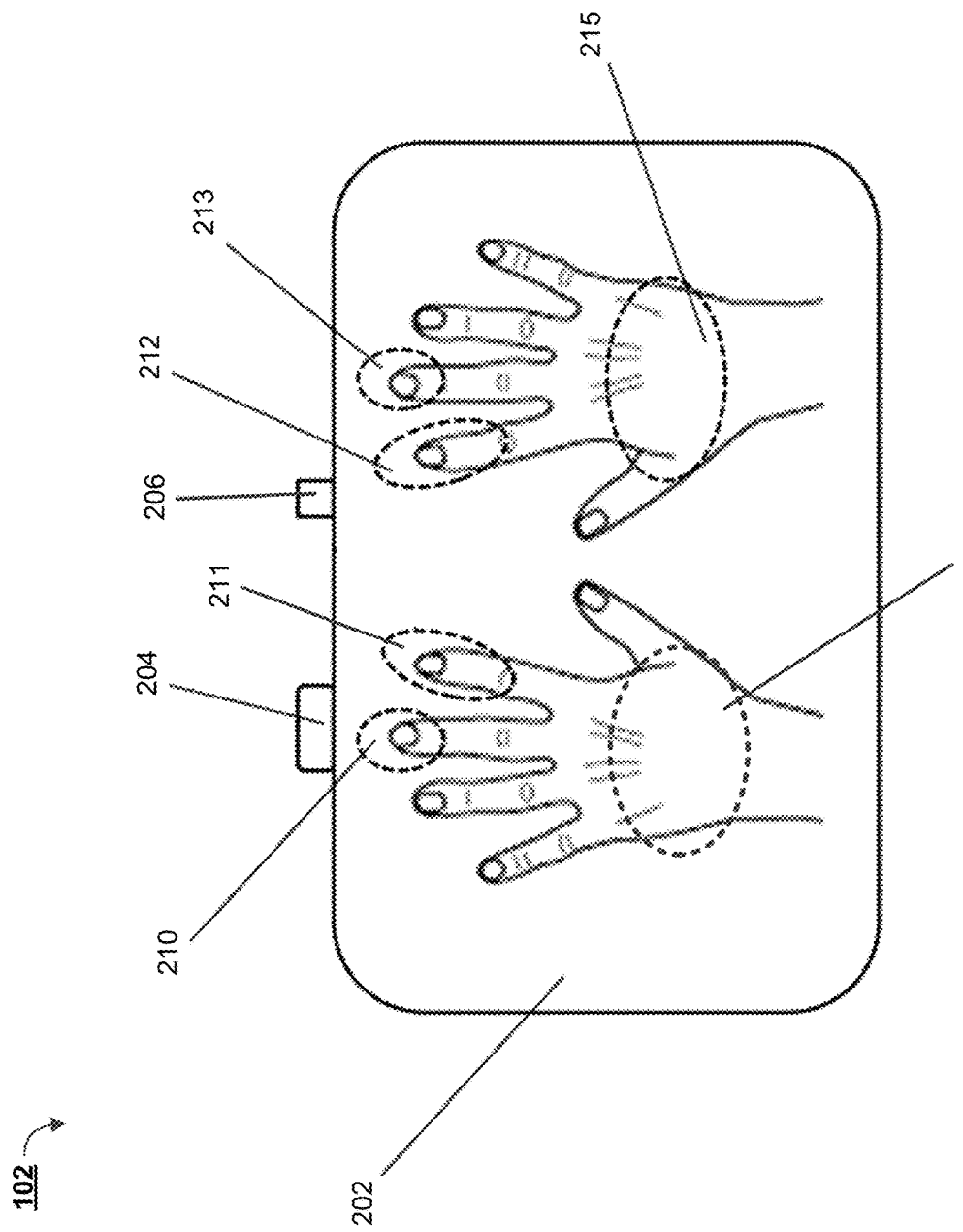
FIG. 2A illustrates a functional block diagram of the sensor device of FIG. 1, in accordance with some example embodiments.
Figure 2B:
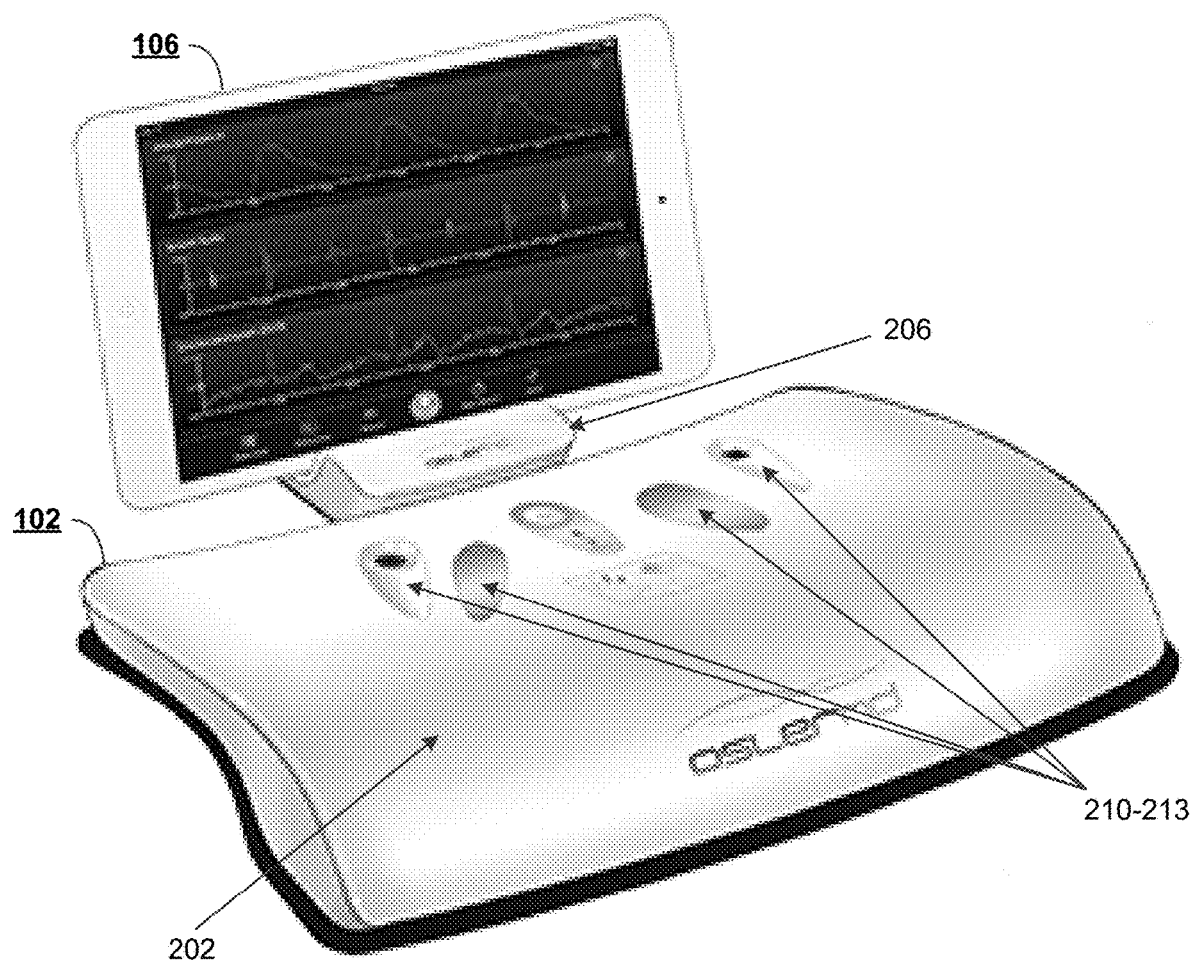
FIG. 2B illustrates an example of the sensor device and computing device of FIG. 1, in accordance with some example embodiments.

FIG. 2A illustrates a functional block diagram of the sensor device 102 of FIG. 1, in accordance with some example embodiments. As illustrated, the sensor device 102 may include a surface 202, a first input module 204, a second input module 206, and one or more sensors 210-215. One or more of the sensors 210-215 may be configured to capture information based on a portion of a user's hand, and the captured information can be processed according to signal and/or data processing algorithms. In some aspects, the surface 202 may be a plastic, metal, glass, or other covering, which may be designed to allow for a comfortable and/or secure placement of a user's hands on the sensor device 102. For example, FIG. 2B illustrates an example embodiment of the sensor device 102 where the surface 202 is curved and/or contoured in shape to allow for the placement of the user's hands on the curved portion, and also contains recessed portions which contain the sensors 210-213 so that the user's fingers can stay in place with less effort.

Referring back to FIG. 2A, as noted above, the sensors 210-213 may include many different forms of sensors. In an example embodiment, sensor 210 includes an peripheral capillary oxygen saturation (SpO2) sensor, sensors 211 and 212 include electrocardiography (ECG) sensors, and/or sensor 213 includes an infrared (IR) sensor. In accordance with related embodiments, the user's left middle finger may be used to determine the user's oxygen saturation and/or heart/pulse rate based on measurements taken by the sensor 210, the user's left index finger may be used to determine an ECG waveform, the user's pulse rate, and/or the user's respiration rate based on measurements taken by the sensors 211 and/or 212, and the user's right middle finger may be used to determine an arterial pressure waveform and/or a cardio audio waveform based on measurements taken by the sensor 213.

In various embodiments, the sensor device 102 may utilize one or both of the first and second input modules 204 and 206 to communicate with another device (or other devices), to receive power, and/or the like. For example, the sensor device 102 may optionally receive inputs from auxiliary/external tethered sensors for additional vital sign information, such as temperature, weight, cuff blood pressure, glucometer, and/or the like. Similarly, the sensor device 102 may communicate with the computing device 106 via one or more of the input modules 204 or 206. In some aspects, one or both of the input modules 204 or 206 may be a universal serial bus (USB) connection or some other data connection. Although some operations are described as being wired, wireless communication is also possible, depending upon the device with which the sensor device 102 is communicating. In some aspects, information transmitted to/from the sensor device 102 may be encrypted.

In some aspects, one or both of the sensors 214 and 215 may be utilized to obtain identification about the user. For example, one or both of the sensors may capture information about a user's palm print, which may be used to uniquely identify the user. Therefore, in some embodiments, a user may be allowed to place both hands on top of the sensor device 102, which in turn measures multiple vital signs at the same time and/or identifies the user. In some embodiments, biometric and/or health information obtained from one or more of the sensors 210-215 may be used to define and/or obtain an aggregate signature for identification of the user. The resulting measurements may be displayed to the user, for example, via the computing device 106. In some embodiments, aggregate health information may be used to characterize a medical condition of a person.

In various embodiments, the computing device 106 may utilize a software application to display the sensor readings and/or vital sign information. For example, the sensor device 102 may be in communication with the computing device 106 running the software application, and the software application may be used to control/direct the sensor device 102 to some degree (e.g., to turn on/off one or more of the sensors 210-215). In some aspects, the computing device 106 may be configured to transmit the vital sign information to a secure cloud storage via the network 110 or provide the vital sign information locally to the database 108. In some aspects, the vital sign information can be attached to the user's health records, processed in post-collection analysis algorithms (e.g., based on the user's health history), provided for further analysis by health and medical professionals, and/or the like.

Although specific measurements are described with respect to specific fingers, specific sensor types, and specific sensor locations other combinations are possible. For example, one of the sensors 210-213 may additionally or alternatively be used to obtain a user's fingerprint and/or one of the sensors 214 or 215 may be used to obtain oxygen saturation, heart/pulse rate, respiration, an ECG waveform, an arterial pressure waveform, and/or a cardio audio waveform.

Figure 3:
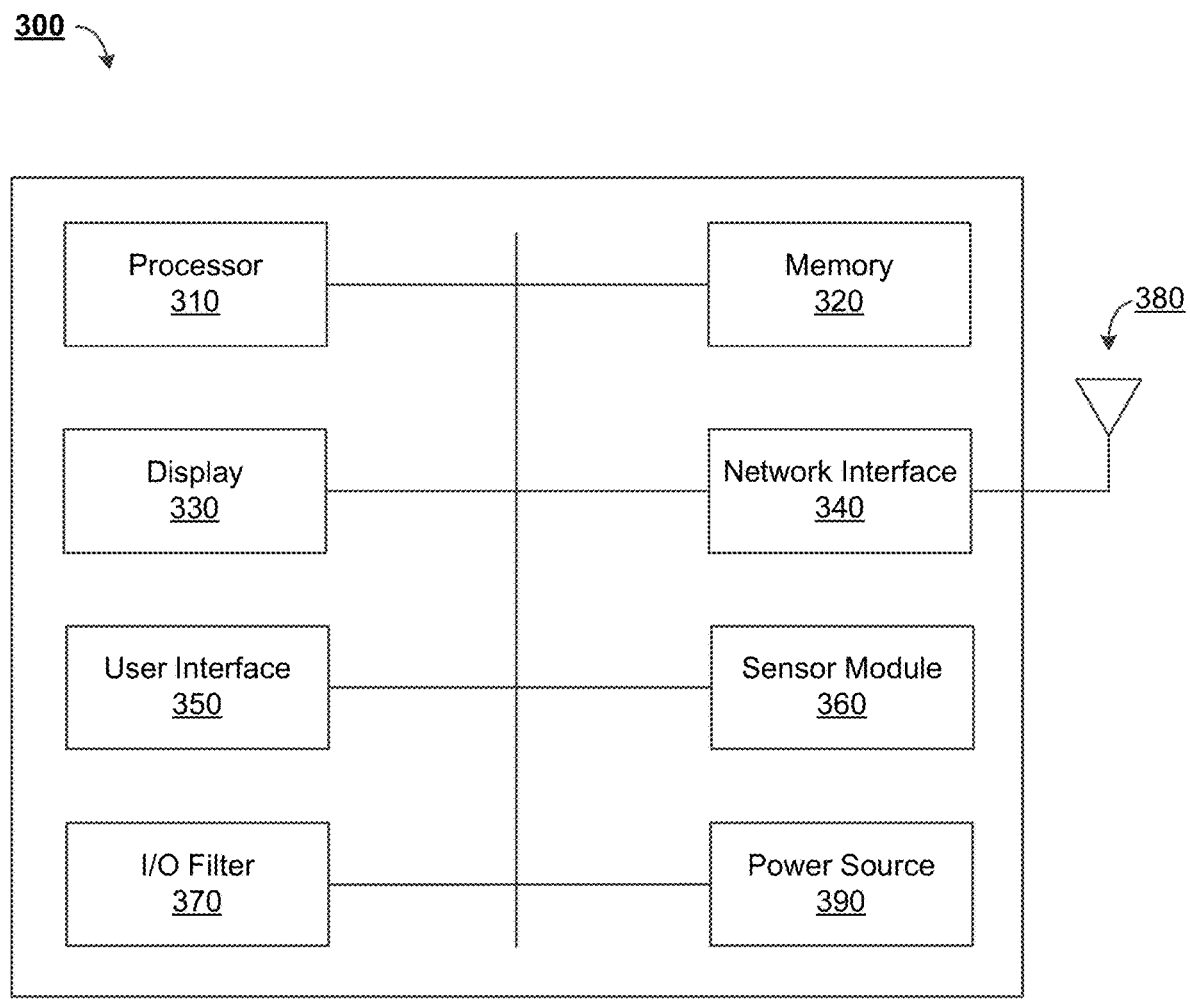
FIG. 3 illustrates an example of a computing apparatus which may be used to implement one or more of the described devices and/or components, in accordance with some example embodiments.

FIG. 3 illustrates an example computing apparatus 300 which may be used to implement one or more of the described devices and/or components, in accordance with some example embodiments. For example, at least a portion of the computing apparatus 300 may be used to implement the sensor device 102, the computing device 106, and/or one or more of the user devices 104. Computing apparatus 300 may perform one or more of the processes described herein.

As illustrated, computing apparatus 300 may include one or more processors such as processor 310 to execute instructions that may implement operations consistent with those described herein. Apparatus 300 may include memory 320 to store executable instructions and/or information. Memory 320 may include solid-state memory, solid-state disk drives, magnetic disk drives, or any other information storage device. In some aspects, the memory 320 may provide storage for at least a portion of a database. Apparatus 300 may include a network interface 340 to a wired network or a wireless network, such as the network 110 of FIG. 1. Wireless networks may include WiFi, WiMax, and cellular networks (2G/3G/4G/5G), and/or any other wireless network. In order to effectuate wireless communications, the network interface 340, for example, may utilize one or more antennas, such as antenna 380.

Apparatus 300 may include one or more user interface, such as user interface 350. The user interface 350 can include hardware or software interfaces, such as a keyboard, mouse, or other interface, some of which may include a touchscreen integrated with a display 330. The display 330 may be used to display visual representations of health information (e.g., vital sign statistics), provide prompts to a user, receive user input, and/or the like. In various embodiments, the user interface 350 can include one or more of the peripheral devices described herein and/or the user interface 350 may be configured to communicate with these peripheral devices.

In some aspects, the user interface 350 may include one or more of the sensors described herein. The operation of these sensors may be controlled at least in part by a sensor module 360. The apparatus 300 may also comprise and input and output filter 370, which can filter information received from the sensors or other user interfaces, received and/or transmitted by the network interface, and/or the like. For example, signals detected through the sensors can be passed through the filter 370 for proper signal conditioning, and the filtered data may then be passed to the microcontroller sensor module 360 and/or processor 310 for validation and processing (e.g., before transmitting results via the network interface 340). The apparatus 300 may be powered through the use of one or more power sources, such as power source 390. As illustrated, one or more of the components of the apparatus 300 may communicate through a system bus.

Figure 4A:
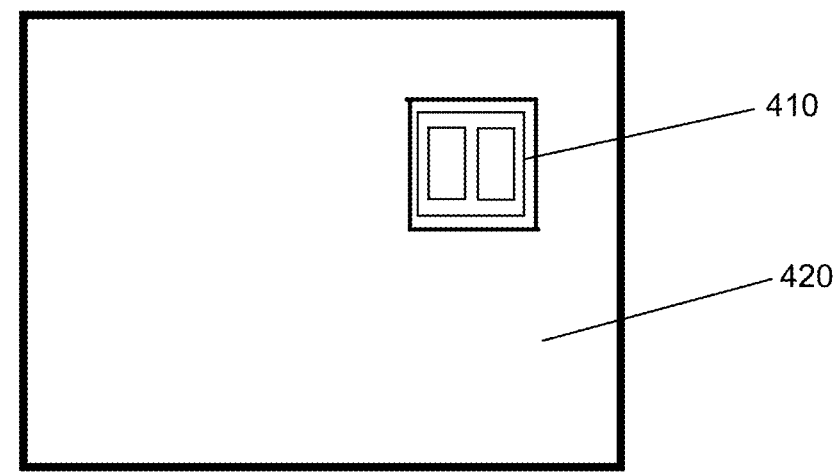
FIG. 4A illustrates an aerial view of an example of a sensor which may be used for determining vital signs, in accordance with some example embodiments.

FIG. 4A illustrates an aerial view of an example sensor component 400 which may be used for determining vital signs, in accordance with some example embodiments. As illustrated, the sensor component 400 may include a sensor portion 410 and a surface portion 420. In various embodiments, the sensor portion 410 can include one or more physical sensors, such as an infrared sensor. The surface portion 420 may be used such that a user's finger remains stationary while the sensor portion 410 is used to collect information from the finger.

Figure 4B:
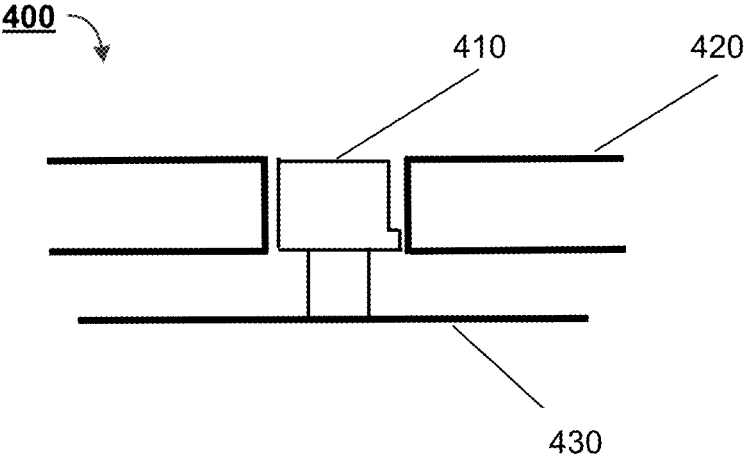
FIG. 4B illustrates a side view of an example of a sensor which may be used for determining vital signs, in accordance with some example embodiments.

FIG. 4B illustrates a side view of the sensor component 400 of FIG. 4A, in accordance with some example embodiments. As illustrated, the sensor portion 410 may be positioned between two opposite, interior surfaces of the surface portion 420 (e.g., inset). In some aspects, the sensor portion 410 may be flush with the surface portion 420, slightly protruding above the level of the surface portion 420, and/or slightly recessed to a point that is lower than the surface portion 420. As further illustrated, the sensor component 400 can contain a base 430 which supports the sensor portion 410. In various embodiments, the base 430 may include circuitry configured to obtain data from the sensor portion 410 for analysis. For example, the base 430 can include a printed circuit board (PCB), and/or the sensor portion 410 may be electrically attached by the leads to the base 430. The base 430 may include additional circuitry to collect the output of the sensor, portion 410 digitize it, and/or format the resulting digitized information. This information may be analyzed and/or transmitted to another device, such as the computing apparatus 106, and or a cloud server.

In some aspects, the sensor portion 410 may be fixed in place or may be moveable (e.g., may be arranged so that it can be pushed down). In some aspects, the surface portion 420 and/or the base 430 may be considered a mechanical platform. In various embodiments, the sensor portion 410 can include a reflective object sensor.

Figure 4C:
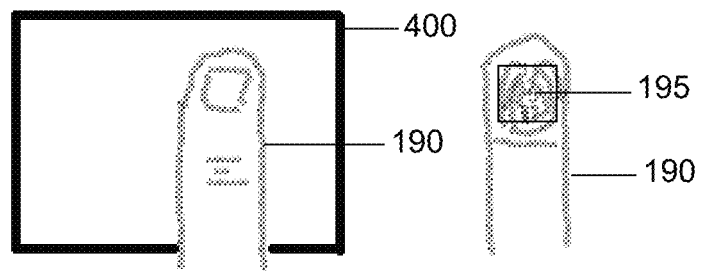
FIG. 4C illustrates an example use of a sensor for determining vital signs, in accordance with some example embodiments.

FIG. 4C illustrates an example use of the sensor component 400 for determining vital signs, in accordance with some example embodiments. As illustrated, a user may place their finger 190 on sensor component 400. In some aspects, the finger 190 may be one of the user's middle fingers or index fingers. In some embodiments, the user may place the finger-tip 195 of their finger 190 directly on top of the sensor portion 410 so that the sensor portion 410 may collect data relating to the user's vital signs. In some aspects, the finger-tip 195 includes the center part of the fingerprint area of the user's finger. The user's finger 190 or finger-tip 195 may cover the sensor portion 410, which transmits IR light and/or responds to the reflection of the signal off of the finger 190. In various embodiments, additional or alternative portions of a user's body where an artery is close to the skin may be used to obtain measurements described herein.

Figure 4D:
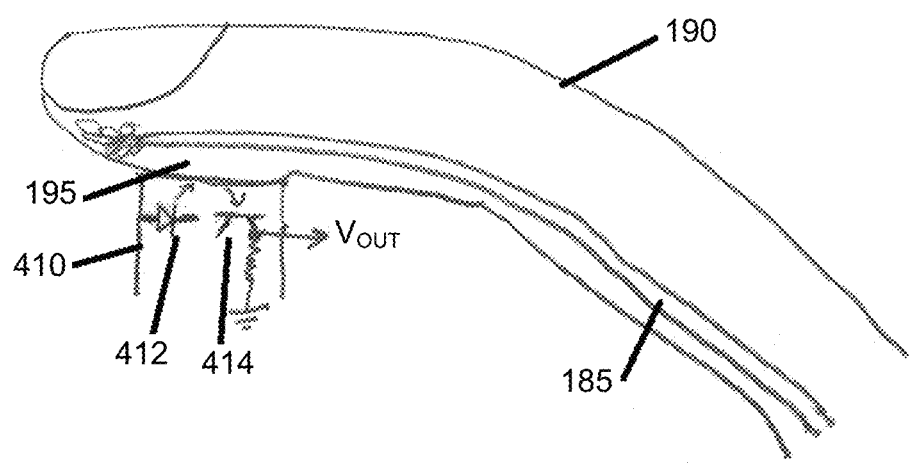
FIG. 4D illustrates an example of a diagram of operation of the sensor for determining vital signs, in accordance with some example embodiments.

For example, FIG. 4D illustrates an example diagram of IR sensing in operation, in accordance with some example embodiments. As illustrated, the sensor portion 410 can include an LED 412 and phototransistor 414. In various embodiments, the LED 412 is used to transmit IR light onto the user's finger-tip 195, and/or the phototransistor 414, based upon the reflection, is configured to output a voltage $V_{OUT}$ proportional to the displacement of the reflection caused by digital arterial pressure. Specifically, the pulse pressure from the digital artery 185 in the finger 190 causes a reflective displacement between the IR light emitting diode 412 and the phototransistor 414 from the surface of the skin that results in a proportional voltage output $V_{OUT}$ corresponding to the time domain signal from which a digital arterial pressure and/or a digital audio can be extracted.

Figure 5A:
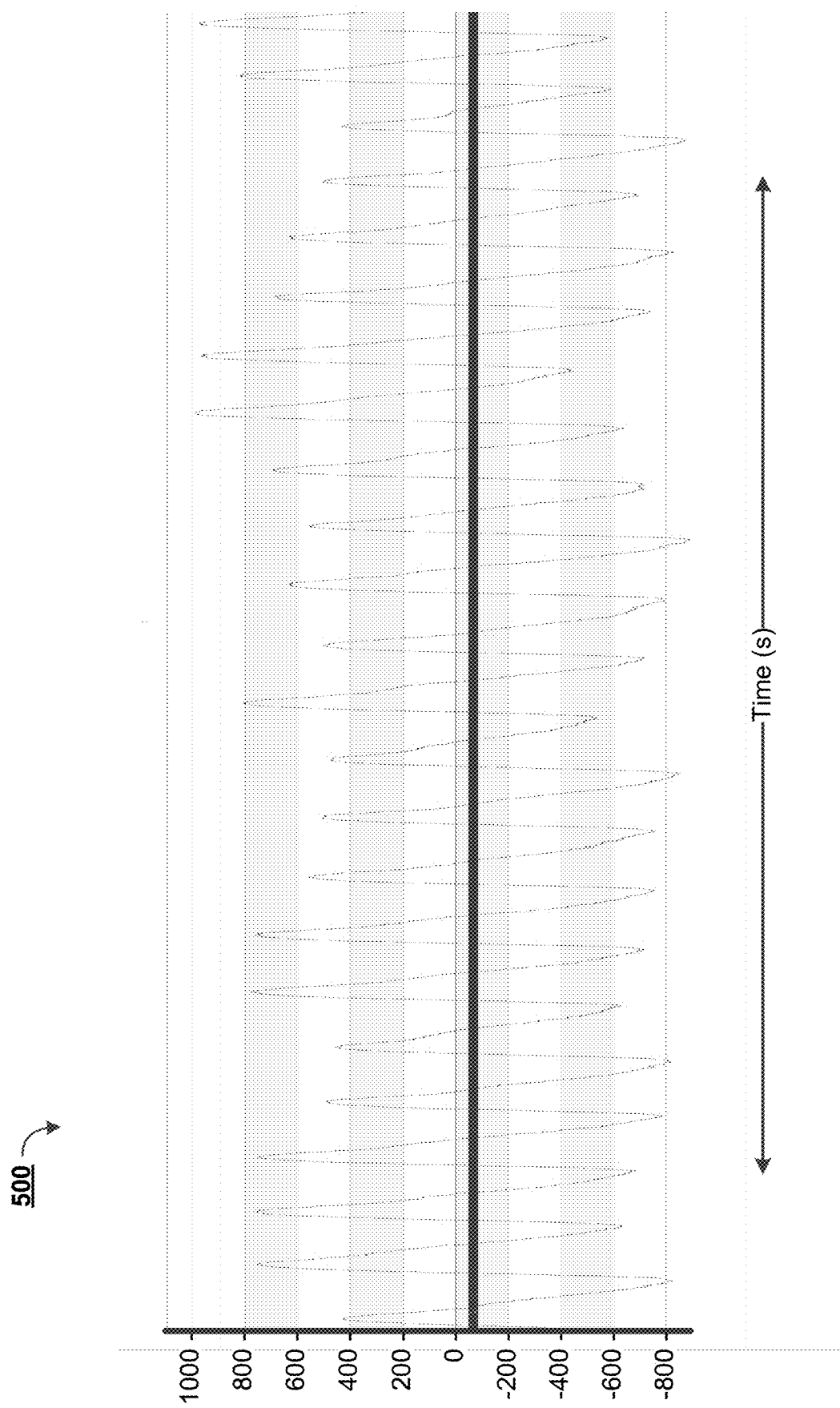
FIG. 5A illustrates an example of an arterial pressure waveform, in accordance with some example embodiments.

In some embodiments, the output voltage $V_{OUT}$ is amplified and/or conditioned with a low-pass filter and/or high-pass filter to produce an electrical signal that correlates to arterial pressure. The filtered output voltage $V_{OUT}$ can thereby include a waveform that is representative of the pressure, over time, of the digital artery 185. An example arterial pressure waveform 500 is illustrated in FIG. 5A, which spans the time frame of approximately twenty seconds.

Figure 4E:
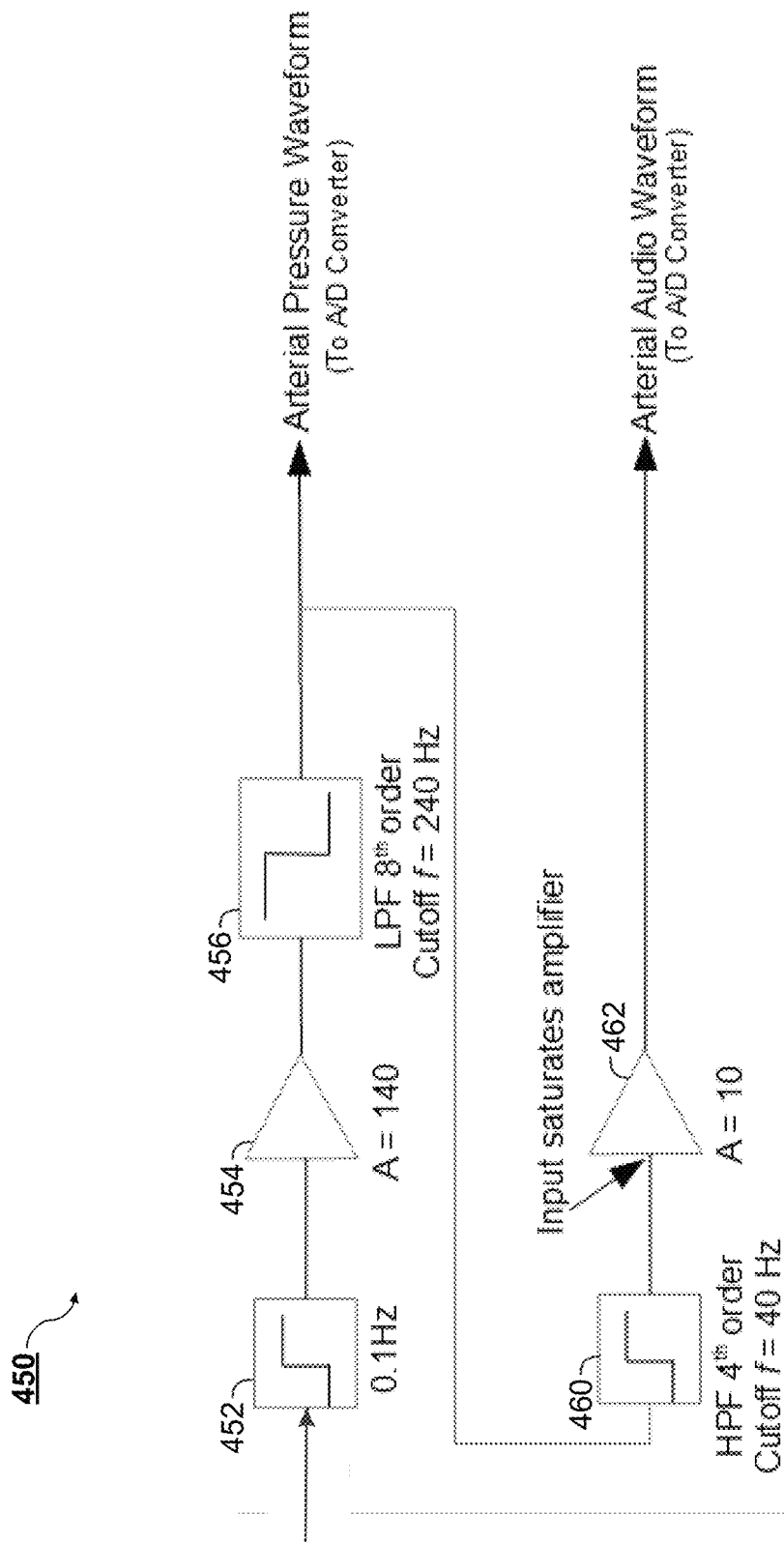
FIG. 4E illustrates an example of a diagram of a circuit for obtaining an arterial pressure waveform and/or arterial audio waveform, in accordance with some example embodiments.

FIG. 4E illustrates an example of a diagram of a circuit 450 for obtaining an arterial pressure waveform and/or arterial audio waveform, in accordance with some example embodiments. As noted above, in some aspects, an audio waveform for the digital artery 185 may additionally or alternatively measured. For example, in some aspects, low-pass and/or high-pass filtering may be performed on the output voltage $V_{OUT}$ to produce a voltage corresponding to the amplitude of the digital arterial pressure audio waveform. Overdriving an audio amplifier can produce visible pulses coincident with cardiac events, producing a waveform similar to a phonocardiogram. These pulses can identify the beginning of a Systole and/and or Diastole. Thus, a one or more of the arterial pressure, ECG, and/or the audio output can be used determine the phases of the cardiac cycle.

For example, a way to determine the audio waveform can include feeding the output of the IR sensor into a high-pass filter (HPF) circuit 452. As illustrated, HPF circuit 452 can be configured to remove DC to 0.1 Hz. The high-pass-filtered output may then be amplified via an amplifier 454 with a gain of 140 dB. The amplified output may then be provided to a low pass filter (LPF) circuit 456. As illustrated, the LPF circuit 456 can be an 8th order LPF with a cutoff frequency of 240 Hz. The resulting, low-pass-filtered output may be indicative of the arterial pressure waveform, which can be fed to an analog-to-digital (A/D) converter to be digitized for further processing as described herein.

Figure 5B:
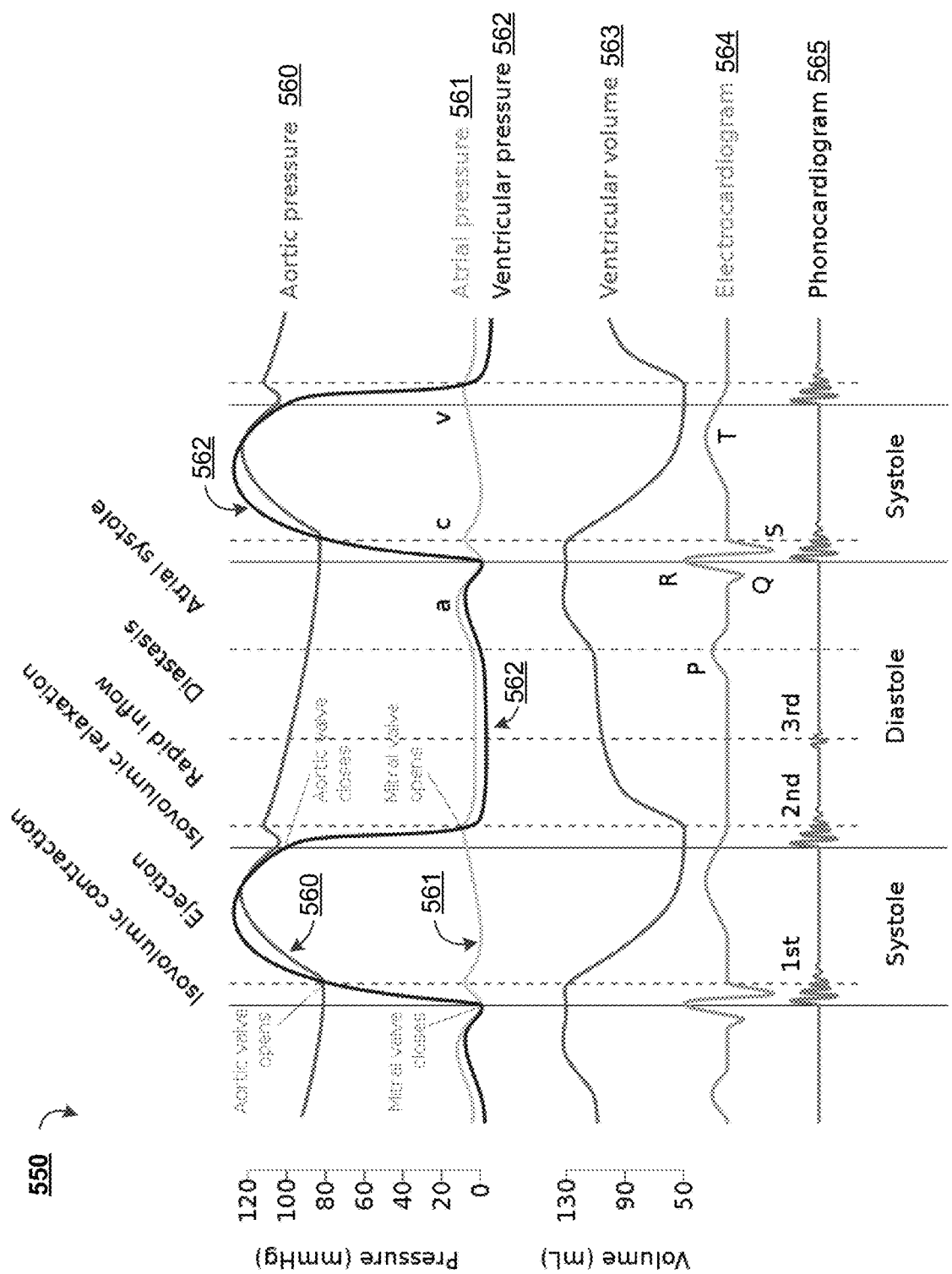
FIG. 5B illustrates example timing diagram of cardiac event waveforms, in accordance with some example embodiments.

In some aspects, the filtered output of the LPF circuit 456 may also be provided to another HPF circuit 460. As illustrated, the HPF circuit 460 may be a $4^{th}$ order HPF with a cutoff frequency of 40 Hz. The high-pass-filtered output may then be provided as an input to an amplifier 462, which may utilize a gain of 10 dB (or more). Amplifying this signal with the amplifier can result in the amplifier 462 being saturated. This may cause a ringing with sharp signal transitions fed to it. The resulting, amplified output may be indicative of the arterial audio waveform, which can be fed to an analog-to-digital (A/D) converter to be digitized for further processing as described herein. Although specific values are illustrated and described, other values may be utilized. For example, to get a less saturated (e.g., clean) audio signal or phonocardiogram, the gain of the amplifier 454 and/or the amplifier 462 can be decreased. With the arterial pressure waveform as input in this configuration, a signal similar to the phonocardiagram signal waveform 565 illustrated in the Wiggers diagram 550 of FIG. 5B may be generated.

The Wiggers diagram 550 illustrates a timing diagram of an aortic pressure waveform 560, an atrial pressure waveform 561, a ventricular pressure waveform 562, a ventricular volume waveform 563, an electrocardiogram signal waveform 564, and a phonocardiogram signal waveform 565. In some embodiments, the arterial pressure waveform described herein can be a waveform resulting from the superposition of each of the aortic pressure waveform 560, the atrial pressure waveform 561, and/or the ventricular pressure waveform 562. The electrocardiogram signal waveform 564 may correspond to a signal obtained from an ECG sensor, as described herein.

As noted above, the configuration of the circuit 450 of FIG. 4E can be used to generate a signal similar to the phonocardiagram signal waveform 565. While the signal generated by the circuit 450 may not be a clearly audible phonocardiagram signal, the ringing transitions may be used for processing and/or analysis, as they can be coincident with other cardiac event timings as shown in the Wiggers diagram 550. Such cardiac event timings can include one or more of an aortic valve opening or closing, a mitral valve opening or closing, isovolumetric contraction or relaxation, ejection, rapid inflow, diastasis, and/or atrial systole. Thus, in some aspects, one or more of the arterial pressure waveform, the arterial audio waveform, and or the ECG waveforms may be used individually or in combination with each other to extract the timing and/or the magnitude of cardiac events. Such extraction methods may provide non-invasive systems and methods for determining vital signs, such as determining a user's blood pressure through a sensor without the use of a cuff. Other measurements related to relative blood pressure and/or blood pressure variations over time may additionally or alternatively determined.

Referring back to FIG. 4E, the measured and/or filtered signals can be sampled with an A/D converter (e.g., within the PCB 430), to produce a stream of integers that can be plotted to display resulting waveforms of arterial pressure and/or arterial pressure audio. This data may be collected from the output of the A/D by processor circuitry (which may be implemented at, our coupled to, the PCB 430). In some aspects, the data may be formatted by the sensor device 102 and/or transmitted to the computing device 106. In some embodiments, the sensor device 102 and/or the computing device 106 may include software (e.g., an application) that plots the arterial pressure waveform and/or the arterial audio waveform for viewing by the user. The resulting waveforms may be recorded, stored, and relayed, by the sensor device 102 and/or computing device 106, to another device, such as a remote server coupled to the Internet (for example, a cloud-based server/computing device). In some aspects, the sensor device 102 and/or the computing device 106 may be configured to determine one or more of the user's vital signs, as described herein.

Figure 6A:
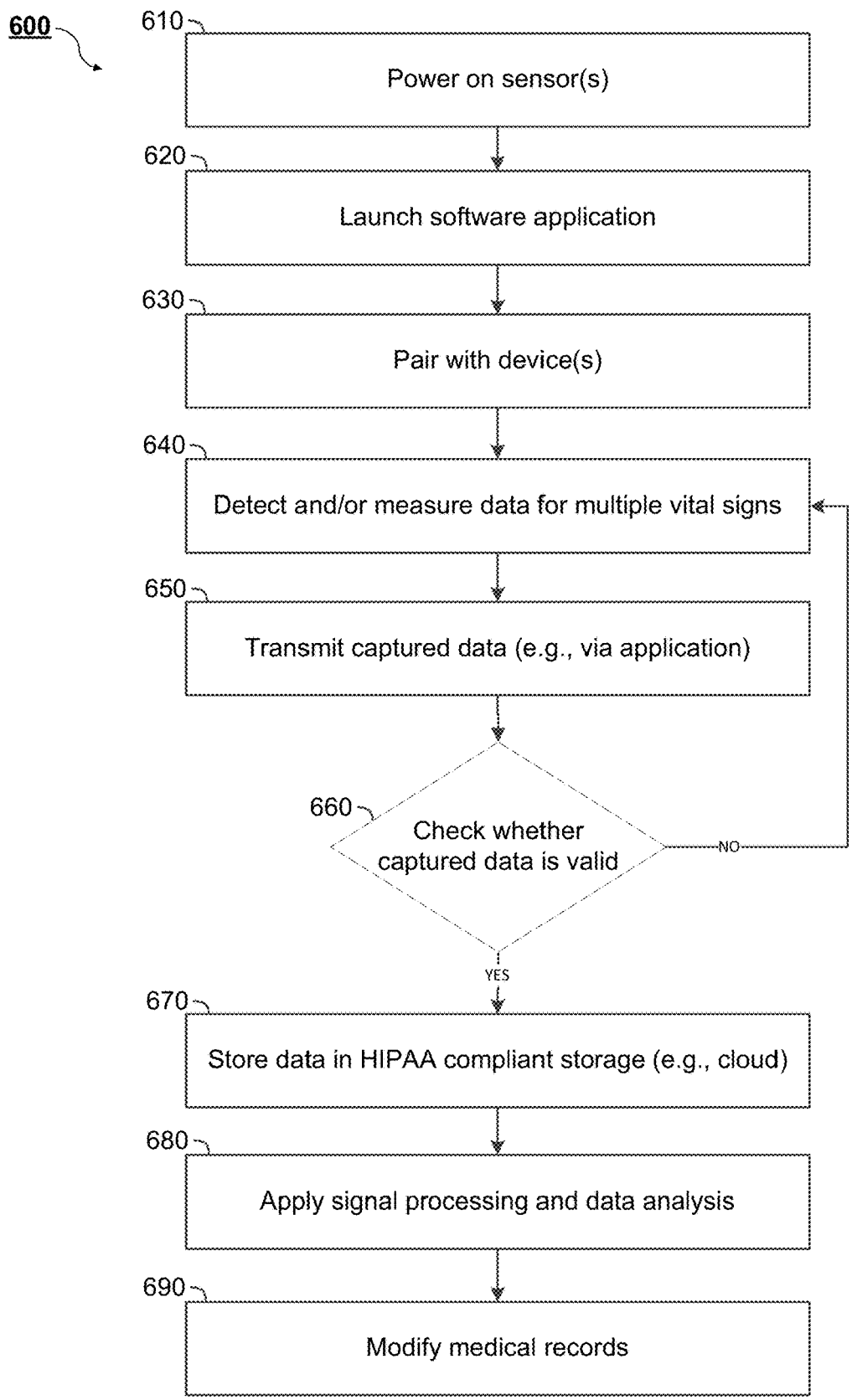
FIG. 6A illustrates an example of a method of using a sensor device to for determining multiple vital signs, in accordance with some example embodiments.

FIG. 6A illustrates an example method 600 of using a sensor device for determining multiple vital signs, in accordance with some example embodiments. In some embodiments, the sensor device 102 and/or the computing device 106 of FIG. 1 may be utilized as part of the method 600. Although a specific sequence of operations of method 600 are illustrated and described with respect to particular devices and/or components, in various embodiments, not all of operations may be present, additional operations may be present, the order of the operations may alter, and/or the operations may be performed by different devices and/or components.

As illustrated, method 600 may begin at operational block 610, where the sensor device 102, for example, is powered on. Powering on the sensor device 102 may include powering on one or more of the sensors 210-215 described herein. Method 600 may proceed to operational block 620 where the computing device 106, for example, may launch application software. Method 600 may then proceed to operational block 630 where the sensor device 102, for example, may pair with the computing device 106, for example. In some aspects, the pairing may occur via a Bluetooth connection, a USB connection, and/or the like. In various embodiments, the pairing and/or connection between devices may be automatic.

Method 600 may then proceed to operational block 640, where the sensor device 102, for example, starts detecting and measuring data for the determination of multiple vital signs. In various embodiments, this data may be measured through one or more of a user's fingertips. Method 600 may proceed to operational block 650 where the sensor device 102, for example, transmits captured data to the computing device 106. Additionally or alternatively, the computing device 106 may transmit the data over the network 110 to another device for storage and/or analysis. As illustrated, this data can be transmitted through the use of the application running on the computing device 106. As described herein, additional information from peripheral devices may be used in conjunction with data obtained from the sensors.

Method 600 may then proceed to operational block 660 where the sensor device 102 (and/or the computing apparatus 106), for example, evaluates whether the detected data is valid or not. In some aspects, the data validation process can be achieved through correlation and calculation of multiple heart rate measurements from the SPO2, ECG waveform, and peripheral arterial pressure waveform. For example, a valid range of heart rate (e.g., minimum to maximum) may be predefined (e.g., based on the user, based on other people with the same/similar health, and/or based on a desired rate). As heartrate can be obtained from all three waveforms (e.g., SpO2, ECG, and arterial pressure) the measured heart rate from all three can be calculated and compared with range, and then compared to each other to evaluate the proper finger placement (e.g., two of the measurements are within the range but a third is not, indicating that the finger placed over the associated sensor is not properly placed). If data is determined to be invalid, this can indicate that the user's fingers are not correctly placed on the sensors. In this case, method 600 may return to operational block 640. Additionally or alternatively, the sensor device 102 and/or the computing device may provide an error message.

If the data is instead determined to be valid, method 600 may next proceed to operational block 670 where the computing device 106, for example, stores the data in a secure storage device (which may be compliant with Health Insurance Portability and Accountability Act (HIPAA) or other privacy regulations). For example, the computing device 106 may store the data in a locally accessible database 108 and/or another device which received the data over the network 110 may store the data in a database accessible to that device. Method 600 may then proceed to operational block 680, where the computing device 106, for example, may apply signal processing and/or algorithms for analysis of the stored data. Method 600 may next proceed to operational block 690, where the computing device 108, for example, may control (e.g., update, revise, or the like) the user's medical records based on the stored data. Additionally or alternatively, a device which receives the data from the computing device 108 may perform one or both of operational blocks 680 and 690.

As a non-limiting example of a benefit, the use of method 600 may provide for the integration of multiple sensors into one apparatus, a non-intrusive method of sensing a person's vital signs, the ability to detect, measure, and/or wirelessly transmit collected data from onboard and auxiliary/external sensors under thirsty seconds, and/or collecting and correlating data via a user's finger or palm print unique biometric identification, without requiring any manual or operational calibration.

Figure 6B:
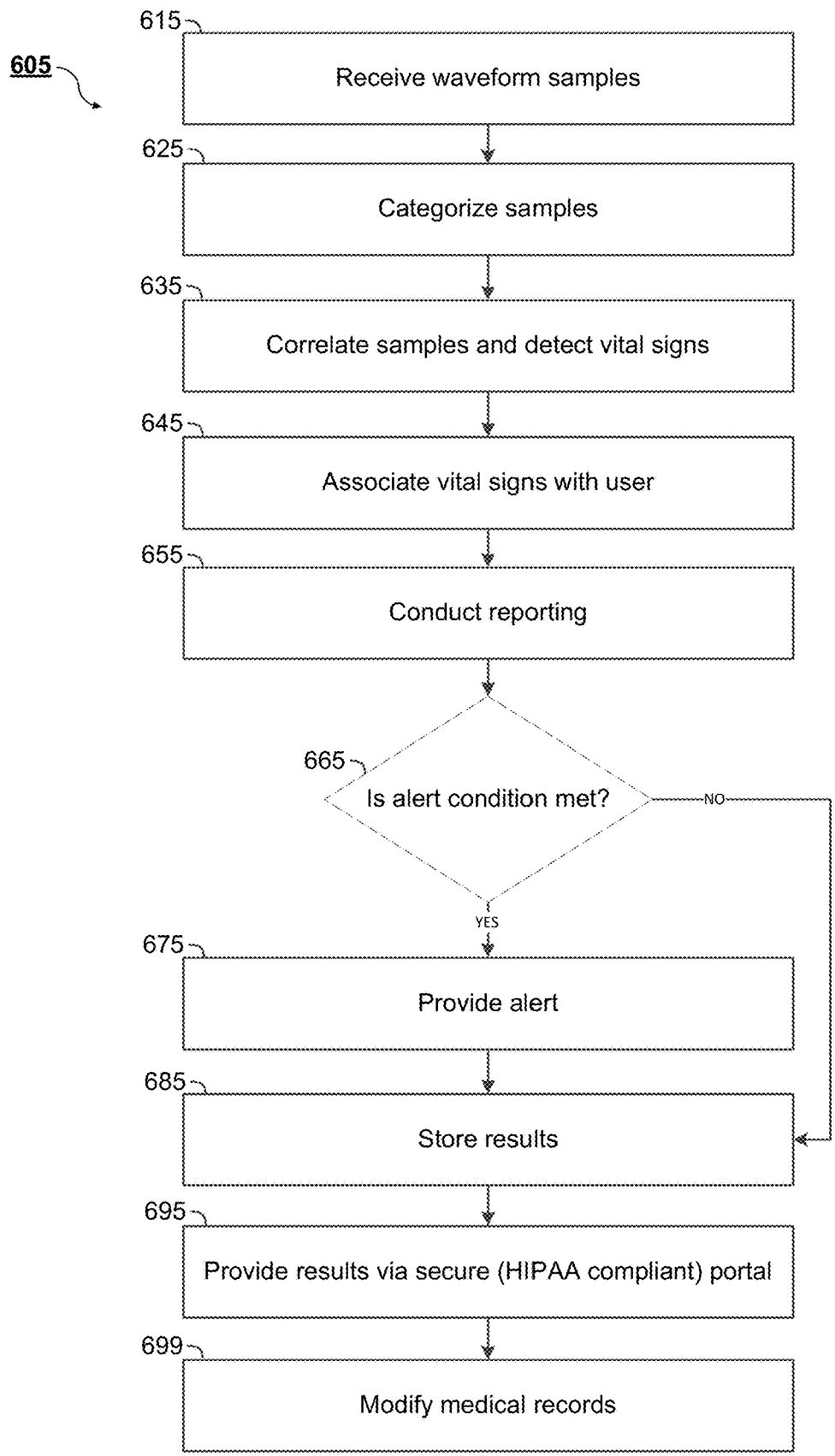
FIG. 6B illustrates an example of a method of determining one or more vital sign, in accordance with some example embodiments.

FIG. 6B illustrates an example method 605 for collecting vital sign information. In some embodiments, the sensor device 102, the computing device 106, and/or one or more of the client devices 104 of FIG. 1 may be utilized as part of the method 605. Although a specific sequence of operational blocks of method 605 are illustrated and described with respect to particular devices and/or components, in various embodiments, not all of operations may be present, additional operations may be present, the order of the operations may alter, and/or the operations may be performed by different devices and/or components. In some aspects, one or more of the operations (or a portion thereof) of method 600 may be integrated into method 605.

As illustrated, method 605, may start at operational block 615 where the computing device 106, for example, receives waveform (e.g., arterial pressure waveform) samples. In some aspects, these waveform samples may be received from a sensor device 102. In some aspects, the waveform samples may be received via a user's finger, such as a middle index, placed over a sensor, as discussed herein. In some aspects, before method 605 begins, the computing device may wait until high enough quality samples are received. Once this is achieved, the sample recording process can start, either automatically or manually by the operator.

Method 605 may next proceed to operational block 625 where the computing device 106, for example, categorizes the waveform samples. In some embodiments, the waveform samples may be categorized according to distinct phenomenon areas to analyze, such as heart rate variability, pulse pressure, arterial elasticity, and/or fluid volume status. In some aspects, heart rate variability can relate to frequency and time duration measurements of the cardiac cycle, pulse pressure can relate to the amplitude of the waveform, arterial elasticity can relate to slope and distortions of the waveform, and/or fluid volume status can relate to ejection ratio calculations and integration integrals of the arterial waveform. Therefore, the waveform samples may be categorized accordingly. In some embodiments, method 605 may wait until a certain amount of time (e.g., 20 seconds, 25 seconds, 30 seconds, or the like) has passed before proceeding to operational block 625.

Method 605 may next proceed to operational block 635 where the computing device 106, for example, correlates the samples and detects vital signs. For example, the computing device 106 may calculate one or more vital signs for a user, based on the categorized data, by using specific algorithms.

Method 605 may next proceed to operational block 645 where the computing device 106, for example, may associate vital signs with a user. In some aspects, the user may be identified by a unique identifier, such as a patient ID, a screen name, social security number, fingerprint, and/or the like.

Method 605 may next proceed to operational block 655 where the computing device 106, for example, conducts reporting. In some aspects, reporting may include transmitting the vital sign information over the network 110 to a client device 104. Reporting may include outputting at least a portion of the results to a reporting function which formats the results for analysis.

Method 605 may next proceed to operational block 665 where the computing device 106, for example, may determine whether an alert condition is met. For example, the computing device 106 may determine whether the user's heart rate or pulse pressure is above a certain threshold. Alert limits may be set by the patient's medical team and/or may suggest a propensity to a specific medical condition that would require immediate attention.

If so, method 605 may next proceed to operational block 675 where the computing device 106, for example, provides an alert. In some aspects, alerts may be customized per user. If an alert condition occurs, specific members of a medical team and/or emergency contact list determined by the alert algorithm, can be immediately notified for example by email, SMS, phone call, and/or the like, depending on how the alert conditions are set up.

Method 605 may next proceed to operational block 685 where the computing device 106, for example, stores the resulting vital sign information. If instead, it is determined at operational block 665 that an alert condition is not met, then method 605 may instead proceed to directly to operational block 685.

Method 605 may next proceed to operational block 695 where the computing device 106, for example, provides results via a secure portal. In some aspects, secure may refer to a portal that is HIPPA compliant. Providing the results via the secure portal can include allowing a user to log into a secure web portal to access their vital sign information (and/or the vital sign information of a patient).

Method 605 may next proceed to operational block 699 where the computing device 106, for example, may modify medical records. For example, if medical records are stored in an electronic format, the computing device 106 may have access to the records, and may add more information, alter information, and/or remove information from a user's medical record.

In various embodiments, one or more of the operations of method 605 may be performed by a device other than the computing device 106. For example, one or more of operational blocks 665-699 may be performed by a cloud computing device, such as a client device 104.

In some aspects, method 605 may additionally or alternatively involve providing a visual display of a peripheral arterial pressure waveform, audio waveform, and/or vital sign information. Similarly, method 605 may include displaying visual indications of whether the signal(s) is/are being received at a quality level needed to make an appropriately accurate interpretation of one or more vital signs.

In some embodiments, the disclosed systems and/or methods may provide an end-to-end solution by encompassing the necessary system components in one platform including the wireless sensor unit, the smart application software, the secure cloud storage, the signal processing and algorithms to calculate and extrapolate various vital signs, and/or the backend data base to provide the final results that can be used by the patients/users or the professionals.

Figure 7:
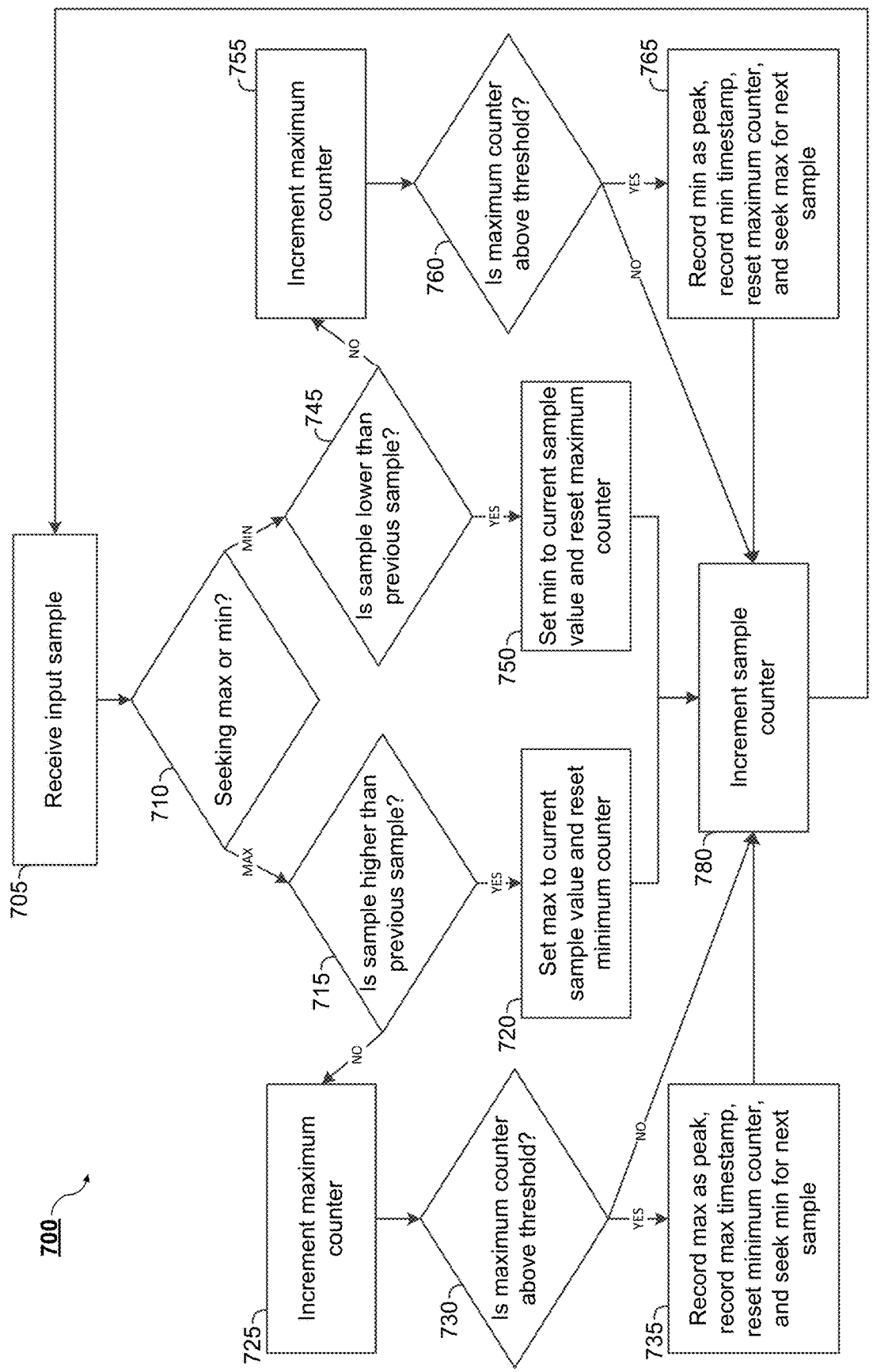
FIG. 7 illustrates an example of a method of determining vital signs based on an arterial pressure waveform, in accordance with some example embodiments.

FIG. 7 illustrates an example method 700 of determining information related to an arterial pressure waveform, in accordance with some example embodiments. In some embodiments, the sensor device 102 and/or the computing device 106 of FIG. 1 may be utilized as part of the method 700. Although a specific sequence of operations of method 700 are illustrated and described with respect to particular devices and/or components, in various embodiments, not all of operations may be present, additional operations may be present, the order of the operations may alter, and/or the operations may be performed by different devices and/or components.

As illustrated, method 700 may start at operational block 705 where a sensor device 102, for example, receives an input sample. In some aspects, the input sample may be a digitized sample of arterial pressure at index "i" (e.g., ap[i]). In various embodiment, each time the index parameter "i" is incremented, a new sample is introduced for processing. Method 700 may next proceed to decision block 710 where the sensor device 102, for example, determines whether a maximum or a minimum peak (or trough) is currently sought. In some embodiments, a parameter "MaxSeek" may be set to "0" if the sensor device 102 is looking for the minimum value and/or may be set to "1" if the sensor device 102 is looking for the maximum value.

If the sensor device 102, for example, determines that it is looking for the max value, process 700 may proceed to decision block 715 where the sensor device 102, for example, determines whether the current sample (e.g., ap[i]) is higher than the previous sample (e.g., ap[i−1]). If so, method 700 may proceed to operational block 720 where the sensor device 102, for example, can set the current max to the current sample value and reset the minimum counter (e.g., a counter of successive minimum evaluations). In some aspects, the minimum counter may be used to determine whether a threshold number of successive points are lower than the current max, signifying that the actual (or approximate) max has already passed. Method 700 may next proceed to operational block 780 where the sensor device 102, for example, increments the sample counter (e.g., increments i). Thereafter, method 700 may return to operational block 705.

If instead, at decision block 715 the sensor device 102, for example, determines that the current sample (e.g., ap[i]) is not higher than the previous sample (e.g., ap[i−1]), then method 700 may instead proceed to operational block 725 where the sensor device 102, for example, may increment the maximum counter (e.g., add one). Thereafter, method 700 may proceed to decision block 730 where the sensor device 102, for example, may determine whether the maximum counter is at or above a threshold. If not, then method 700 may proceed to operational block 780. If instead it is determined that the maximum counter is at or above the threshold, then method 700 may instead proceed to operational block 735. At operational block 735, the sensor device 102, for example may record the current max as the max for the current peak, record the corresponding timestamp for the maximum, reset the minimum counter (e.g., to a value of 0), and/or may seek the minimum for the next sample (e.g., set MaxSeek to equal 0). Thereafter, method 700 may proceed to operational block 780.

If instead, at decision block 710 the sensor device 102, for example, determines that it is looking for a min value, then method 700 may proceed to decision block 745 where the sensor device 102, for example, determines whether the current sample (e.g., ap[i]) is lower than the previous sample (e.g., ap[i−1]). If so, method 700 may proceed to operational block 750 where the sensor device 102, for example, can set the current min to the current sample value and reset the maximum counter (e.g., a counter of successive maximum evaluations). In some aspects, the maximum counter may be used to determine whether a threshold number of successive points are higher than the current min, signifying that the actual (or approximate) min has already passed. Method 700 may next proceed to operational block 780.

If instead, at decision block 745 the sensor device 102, for example, determines that the current sample (e.g., ap[i]) is not lower than the previous sample (e.g., ap[i−1]), then method 700 may instead proceed to operational block 755 where the sensor device 102, for example, may increment the maximum counter (e.g., add one). Thereafter, method 700 may proceed to decision block 760 where the sensor device 102, for example, may determine whether the minimum counter is at or above a threshold. If not, then method 700 may proceed to operational block 780. If instead it is determined that the maximum counter is at or above the threshold, then method 700 may instead proceed to operational block 765. At operational block 765, the sensor device 102, for example may record the current min as the min for the current trough, record the corresponding timestamp for the minimum, reset the maximum counter (e.g., to a value of 0), and/or may seek the maximum for the next sample (e.g., set MaxSeek to equal 1). Thereafter, method 700 may proceed to operational block 780.

In some embodiments, the sensor device 102 may conduct an initialization procedure. For example, upon start-up, the sensor device 102 may evaluate whether the samples taken are increasing, thus approaching a peak, or decreasing, thus approaching a trough. If the sample values are increasing, then the sensor device 102 may determine that it is initially seeking a max (e.g., setting MaxSeek to a value of 1), or vice versa. In some aspects, the minimum counter and/or the maximum counter may both be initialized to a value of 0.

In some embodiments, as long as the integrity of the waveform is intact, the algorithm may be able to correctly evaluate the parameters. If, however, there is an aberration in the signal (e.g., excessive noise or finger movements) where the integrity of the signal is compromised, the resulting calculations may be distorted beyond the ability to calculate. This case can be handled by setting a criteria check for the calculations to be within a specified range (e.g., a range of reasonably expected values). In addition, if the heart rate is calculated redundantly by other sensors (e.g., SpO2 and/or ECG), the calculations may be checked against the IR measurements to determine whether the estimates are within a certain threshold range of each other (e.g., estimates based on IR are a specified percentage away from one or more of the other estimates based on other sensors). If errors or unreliable data are determined to exist, the arterial pressure cycle measurement(s) in question can be removed from the heart rate calculation.

The shape and modulation of the waveform can be effected by a number of cardiac events and disturbances due to such conditions as arterial hardening, heart murmurs, operation of the heart valves, etc. Thus, from the waveform, there are multiple vital signs calculations that can be produced. For example, relative pulse pressure (e.g., the difference between the magnitudes of the systolic blood pressure and the diastolic blood pressure) may be calculated based on the waveform. Although an absolute value of systolic pressure and/or diastolic pressure may not be directly calculated from the waveform in some embodiments, a pulse pressure value, which is the difference between the two values, may be evaluated.

Additionally, heart rate (e.g., beats per minute) may be calculated. In some embodiments, in order to calculate the heart rate, a more traditional method might be to perform a discrete Fourier analysis of the waveform samples to extract the fundamental frequency with DC removed and the lower frequency component(s) which is caused by/correlates with the respiration rate. This fundamental frequency value can be equivalent to the inverse of the temporal value of the cyclic period of the arterial pressure waveform, and may be a close representation of the average value of the heart rate.

Another approach is to find and utilize the length of the period of each cycle by establishing the temporal positions of the start of each repeating cycle. Any arbitrary point on the waveform could be used, however the particular value and/or temporal position of any given peak may be more readily established. From this, one or more additional calculations may be established.

The temporal values of the peak positions can be used to calculate an instantaneous heart rate every cycle where peak[n] is the time stamp in seconds at the first peak, peak[n+1] is the time tamp in seconds at the following peak, and the instantaneous heart rate value HR is equal to [60 seconds/minute÷(peak[n+1]−peak[n]) seconds] in heart beats/minute. Although peaks are described, other related points may additionally or alternatively be used, such as troughs and/or zero-crossing points.

Heart rate fluctuation/variation (e.g., how the rate varies from beat to beat) may also be determined. A human heart rate may normally have some variation, but abnormal variations can be caused by atrial fibrillation, heart murmurs, and/or the like. Therefore, accurately determining this measurement may be beneficial.

If instantaneous heart rate calculations are performed for each observed cycle, heart rate fluctuation can be readily monitored. For example, how the successive values of heart rate vary over the recording series may be monitored/determined. In order to determine the heart rat variations, a maximum heart rate, minimum heart rate, average heart rate, standard deviation, and/or the like may be calculated. In some aspects, the sensor device 102 may be set to monitor a user for longer and/or continuous (e.g., similar to a Holter monitor) monitoring, which may allow for detection of momentary heart fluctuations.

As noted above, respiration rate (e.g., breath cycles per minute) may be calculated. Looking back to the waveform 500 of FIG. 5, a lower frequency component, upon which the arterial pressure cycles are modulated, can be seen. These recorded cycles can have a low frequency offset superimposed on the waveform which corresponds to the respiration rate. So using the same/similar algorithm that is used to calculate the heart rate, the waveform corresponding to a temporal plotted value of the peaks can be processed to determine the fundamental frequency, which may be the value of respiration. In the same/similar manner as in the case of the heart rate calculation the instantaneous frequency may be measured for for each cycle. As in the case of the heart rate calculation, a maximum, a min, an average, a standard deviation, and/or the like may be calculated from the series.

In some aspects, the longer the series of samples collected, the more accurate an average respiration and/or heart rate may be obtained. As the respiration rate is slower more samples may be needed to provide an accurate/reliable calculation compared to heart rate. Therefore, in some embodiments, at least twenty seconds of reliable samples may be recorded to process enough samples for a respiration calculation. The sensor device 102 can be programmed via a user-entered entry to record this waveform for any length of time.

Figure 8:
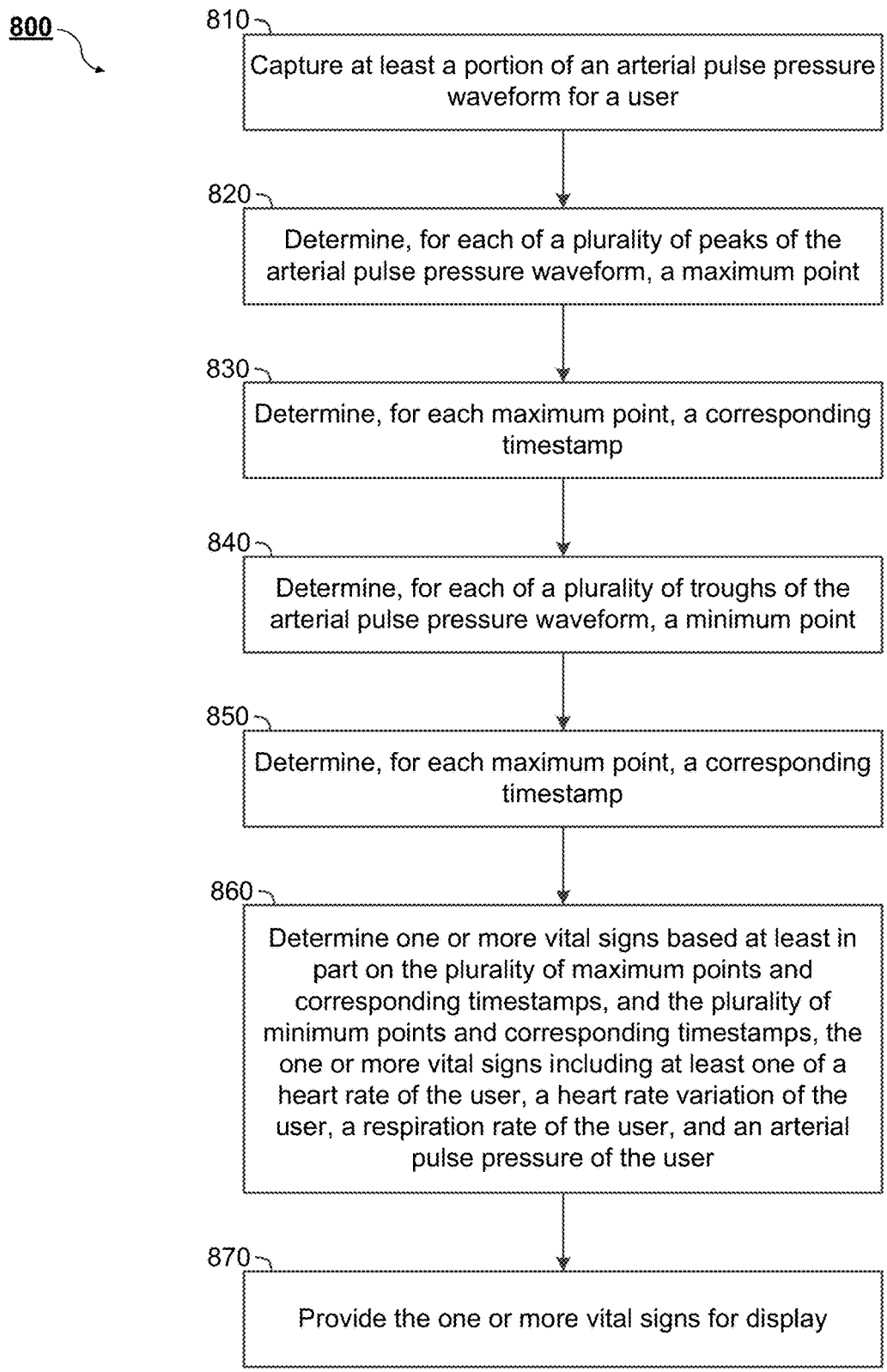
FIG. 8 illustrates an example of a method of using a sensor device to for determining one or more vital sign, in accordance with some example embodiments.

FIG. 8 illustrates a method 800 of calculating one or more vital signs. In some embodiments, the sensor device 102, the computing device 106, and/or one or more of the client devices 104 of FIG. 1 may be utilized as part of the method 800. Although a specific sequence of operations of method 800 are illustrated and described with respect to particular devices and/or components, in various embodiments, not all of operations may be present, additional operations may be present, the order of the operations may alter, and/or the operations may be performed by different devices and/or components.

Method 800 may start at operational block 810 where the sensor device 102, for example, may capture at least a portion of an arterial pulse pressure waveform for a user.

Method 800 may proceed to operational block 820 where the sensor device 102, for example, may determine, for each of a plurality of peaks of the arterial pulse pressure waveform, a maximum point. In some embodiments, determining the maximum points includes determining, for a plurality of subsequent samples of the arterial pulse pressure waveform, whether a current sample is greater in pressure than a prior sample, storing the current sample when the current sample is greater in pressure than the prior sample, determining whether a threshold number of subsequent samples are not greater than the stored sample, and setting the stored sample as the maximum point (e.g., for the current peak (e.g., peak[n])) when the threshold number of subsequent samples are not greater than the stored sample.

Method 800 may proceed to operational block 830 where the sensor device 102, for example, may determine, for each maximum point, a corresponding timestamp. For example, determining the corresponding timestamp may include checking a clock and/or storing the clock value related to the maximum point (e.g., peak[n]).

Method 800 may proceed to operational block 840 where the sensor device 102, for example, may determine, for each of a plurality of troughs of the arterial pulse pressure waveform, a minimum point. In some embodiments, determining the minimum points includes determining, for a plurality of subsequent samples of the arterial pulse pressure waveform, whether a current sample is lower in pressure than a prior sample, storing the current sample when the current sample is lower in pressure than the prior sample, determining whether a threshold number of subsequent samples are not lower than the stored sample, and setting the stored sample as the minimum point (e.g., for the current trough (e.g., trough[n])) when the threshold number of subsequent samples are not lower than the stored sample. Although peaks, troughs, maximum points, and/or minimum points are illustrated and described, other related points may be used. For example, a zero-crossing (rising or falling) pressure point may be determined.

Method 800 may proceed to operational block 850 where the sensor device 102, for example, may determine, for each maximum point, a corresponding timestamp.

Method 800 may proceed to operational block 860 where the sensor device 102, for example, may determine one or more vital signs based at least in part on the plurality of maximum points and corresponding timestamps, and/or the plurality of minimum points and corresponding timestamps, the one or more vital signs including at least one of a heart rate of the user, a heart rate variation of the user, a respiration rate of the user, and an arterial pulse pressure of the user.

Method 800 may proceed to operational block 870 where the sensor device 102, for example, may provide the one or more vital signs for display. In various embodiments, determining the heart rate includes generating a plurality of peak rates by at least subtracting, for each of the plurality of related points (e.g., maximum, minimum, and/or other), the corresponding first timestamp of a most recent related point from the corresponding first timestamp of a current related point. In some aspects, determining the heart rate further includes averaging the plurality of peak rates.

In some embodiments, method 800 may additionally or alternatively include determining an arterial audio waveform based at least in part on the arterial pressure waveform (e.g., through the use of one or more filter and/or one or more amplifier). Method 800 can similarly include determining one or more cardiac events of the user based at least in part on the arterial pressure waveform, the arterial audio waveform, and or an electrocardiography waveform. The one or more cardiac events can include an aortic valve opening or closing, a mitral valve opening or closing, an isovolumetric contraction or relaxation, an ejection, a rapid inflow, diastasis, and/or an atrial systole.

In related embodiments, determining the heart rate variation includes determining a maximum rate from the plurality of peak rates, determining a minimum rate from the plurality of peak rates, and/or determining a standard deviation from the plurality of peak rates. In some embodiments, determining the respiration rate includes determining a fundamental frequency of the arterial pulse pressure waveform.

In some embodiments, the infrared sensor is configured to capture the at least the portion of the arterial pulse pressure waveform from the user's finger via providing signals from a light emitting diode and measuring reflections via a phototransistor. In some embodiments, the sensor device 102, for example, may also include a peripheral capillary oxygen saturation sensor configured to measure oxygen saturation from a user's second finger, and one or more electrocardiography sensors configured to measure an electrocardiography waveform from a user's third finger, wherein the one or more electrocardiography sensors are further configured to measure one or both of the respiration rate and the heart rate from a user's fourth finger.

In some embodiments, the disclosed systems may be used as a platform in broad range of application where there is a need to collect multiple key vital signs simultaneously and seamlessly at local or remote settings. In some embodiments, the disclosed system may be configured into stationary units, or portable/mobile units, or wearable units, or various kiosk units and can include integrated or separated tablet or mobile device for display.

The subject matter described herein may be embodied in systems, apparatus, methods, and/or articles depending on the desired configuration. For example, the systems, apparatus, methods, and/or articles described herein can be implemented using one or more of the following: electronic components such as transistors, inductors, capacitors, resistors, and the like, a processor executing program code, an application-specific integrated circuit (ASIC), a digital signal processor (DSP), an embedded processor, a field programmable gate array (FPGA), and/or combinations thereof. These various example embodiments may include embodiments in one or more computer programs that are executable and/or interpretable on a programmable system including at least one programmable processor, which may be special or general purpose, coupled to receive data and instructions from, and to transmit data and instructions to, a storage system, at least one input device, and at least one output device. These computer programs (also known as programs, software, software applications, applications, components, program code, or code) include machine instructions for a programmable processor, and may be implemented in a high-level procedural and/or object-oriented programming language, and/or in assembly/machine language. As used herein, the term "machine-readable medium" refers to any computer program product, computer-readable medium, computer-readable storage medium, apparatus and/or device (for example, magnetic discs, optical disks, memory, Programmable Logic Devices (PLDs)) used to provide machine instructions and/or data to a programmable processor, including a machine-readable medium that receives machine instructions. Similarly, systems are also described herein that may include a processor and a memory coupled to the processor. The memory may include one or more programs that cause the processor to perform one or more of the operations described herein.

Although a few variations have been described in detail above, other modifications or additions are possible. In particular, further features and/or variations may be provided in addition to those set forth herein. Moreover, the example embodiments described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results. Other embodiments may be within the scope of the following claims.

What is claimed:
1. An apparatus comprising:
a display configured to be accessible by a user;
an infrared sensor coupled with the display configured to at least capture at least a portion of an arterial pulse pressure waveform from a user, the at least a portion of the arterial pulse pressure waveform comprising a plurality of groups of related points, the plurality of groups of related points comprising a plurality of peak points, the plurality of peak points each comprising a maximum pressure value; and
a processor coupled with the display and the infrared sensor, the processor configured to cause operations comprising:
determining whether to calculate the maximum pressure value or a minimum value for each of the plurality of groups of related points;
determining to calculate the maximum pressure value for each of the plurality of groups of related points;
determining the maximum pressure value for each of the plurality of groups of related points and a corresponding first timestamp of the maximum pressure value, wherein the determination of the maximum pressure value comprises:
determining for a current group of the plurality of groups of related points of the arterial pulse pressure waveform, whether a current sample has a current maximum pressure value that is greater than a prior maximum pressure value from a prior within the current group of related points that was previously received by the infrared sensor;
storing the current maximum pressure value when the current maximum pressure value is greater than the prior maximum pressure value; and
setting the stored current maximum pressure value as the maximum pressure value when the current maximum pressure value of a threshold number of samples is not greater than the stored current maximum pressure value;
determining one or more vital signs based at least in part on the maximum pressure values and the corresponding first timestamps;
determining, based on the determined one or more vital signs, that an alert condition is met, the alert condition comprising a vital sign value being greater than or equal to a predefined threshold vital sign value;
providing, based on the determination that the alert condition is met, an alert indicating that the alert condition has been met; and
displaying the one or more vital signs to the user via the display,
wherein the one or more vital signs include a heart rate of the user, a heart rate variation of the user, and a respiration rate of the user.

2. The apparatus of claim 1, wherein determining the heart rate includes generating a plurality of peak rates by at least subtracting, for each of the plurality of groups related points, the corresponding first timestamp of the maximum pressure value of a group of related points from the corresponding first timestamp of the maximum pressure value of an immediately subsequent group of related points.

3. The apparatus of claim 2, wherein determining the heart rate further includes averaging the plurality of peak rates.

4. The apparatus of claim 2, wherein determining the heart rate variation includes:
   determining a maximum rate from the plurality of peak rates;
   determining a minimum rate from the plurality of peak rates; and
   determining a standard deviation from the plurality of peak rates.

5. The apparatus of claim 1, wherein determining the respiration rate includes:
   determining a fundamental frequency of the arterial pulse pressure waveform.

6. The apparatus of claim 1, wherein the processor is further configured to cause operations comprising:
   determining to calculate the minimum value;
   determining, for each of a plurality of troughs of the arterial pulse pressure waveform, the minimum value;
   determining, for each of the minimum values, a corresponding second timestamp; and
   wherein the determining the one or more vital signs is further based at least in part on the plurality of minimum values and the plurality of corresponding second timestamps.

7. The apparatus of claim 1, wherein the infrared sensor is configured to capture the at least the portion of the arterial pulse pressure waveform from the user's finger via providing signals from a light emitting diode and measuring reflections via a phototransistor.

8. The apparatus of claim 7, further comprising:
   a peripheral capillary oxygen saturation sensor configured to measure oxygen saturation from a user's second finger; and
   one or more electrocardiography sensors configured to measure an electrocardiography waveform from a user's third finger.

9. The apparatus of claim 1, wherein the processor is further configured to cause operations comprising:
   determining, based at least in part on the arterial pulse pressure waveform, an arterial audio waveform; and
   determining, based at least in part on the arterial pulse pressure waveform and the arterial audio waveform, one or more cardiac events of the user,
   wherein the one or more cardiac events includes at least one of an aortic valve opening or closing, a mitral valve opening or closing, an isovolumetric contraction or relaxation, an ejection, a rapid inflow, diastasis, and an atrial systole.

10. The apparatus of claim 1, wherein the alert comprises one or more of an email, SMS, and phone call.

11. The apparatus of claim 1, wherein the determination to calculate the maximum pressure value for each of the plurality of groups of related points is in response to the determination of whether to calculate the maximum pressure value or the minimum value.

12. A method comprising:
   capturing, via an infrared sensor coupled with a display configured to be accessible by a user, at least a portion of a current sample of an arterial pulse pressure waveform from the user, the at least a portion of the arterial pulse pressure waveform comprising a plurality of groups of related points, the plurality of groups of related points comprising a plurality of peak points, the plurality of peak points each comprising a maximum pressure value;
   determining, via a processor in communication with the infrared sensor and the display, whether to calculate the maximum pressure value or a minimum pressure value for each of the plurality of groups of related points;
   determining, via the processor, to calculate the maximum pressure value for each of the plurality of groups of related points;
   determining, via the processor, the maximum pressure value for each of the plurality of groups of related points and a corresponding first timestamp of the maximum pressure value, wherein the determination of the maximum pressure value comprises:
      determining for a current group of the plurality of groups of related points of the arterial pulse pressure waveform, whether a current sample has a current maximum pressure value that is greater than a prior maximum pressure value from a prior sample within the current group of related points that was previously received by the infrared sensor;
      storing the current maximum pressure value when the current maximum pressure value is greater than the prior maximum pressure value; and
      setting the stored current maximum pressure value as the maximum pressure value when the current maximum pressure value of a threshold number of samples is not greater than the stored current maximum pressure value;
   determining one or more vital signs based at least in part on the maximum pressure values and the corresponding first timestamps;
   determining, based on the determined one or more vital signs, that an alert condition is met, the alert condition comprising a vital sign value being greater than or equal to a predefined threshold vital sign value;
   providing, based on the determination that the alert condition is met, an alert indicating that the alert condition has been met; and
   displaying the one or more vital signs to the user via the display, wherein the one or more vital signs include a heart rate of the user, a heart rate variation of the user, and a respiration rate of the user.

13. The method of claim 12, wherein determining the heart rate includes generating a plurality of peak rates by at least subtracting, for each of the plurality of groups of related points, the corresponding first timestamp of the maximum pressure value of a group of related points from the corresponding first timestamp of the maximum pressure value of an immediately subsequent group of related points.

14. The method of claim 13, wherein determining the heart rate variation includes:
   determining a maximum rate from the plurality of peak rates;
   determining a minimum rate from the plurality of peak rates; and
   determining a standard deviation from the plurality of peak rates.

15. The method of claim 12, wherein determining the respiration rate includes:
   determining a fundamental frequency of the arterial pulse pressure waveform.

16. A non-transitory computer program product storing instructions which, when executed by at least one hardware data processor, result in operations comprising:
   capturing, via an infrared sensor coupled with a display configured to be accessible by a user, at least a portion of a current sample of an arterial pulse pressure waveform from the user, the at least a portion of the arterial pulse pressure waveform comprising a plurality of groups of related points, the plurality of groups of related points comprising a plurality of peak points, the plurality of peak points each comprising a maximum pressure value;

determining, via a processor in communication with the infrared sensor and the display, whether to calculate the maximum pressure value or a minimum pressure value for each of the plurality of groups of related points;

determining, via the processor, to calculate the maximum pressure value for each of the plurality of groups of related points;

determining, via the processor, the maximum pressure value for each of the plurality of groups of related points and a corresponding first timestamp of the maximum pressure value, wherein the determination of the maximum pressure value comprises:

determining for a current group of the plurality of groups of related points of the arterial pulse pressure waveform, whether a current sample has a current maximum pressure value that is greater than a prior maximum pressure value from a prior sample within the current group of related points that was previously received by the infrared sensor;

storing the current maximum pressure value when the current maximum pressure value is greater than the prior maximum pressure value; and setting the stored current maximum pressure value as the maximum pressure value when the current maximum pressure value of a threshold number of samples is not greater than the stored current maximum pressure value;

determining one or more vital signs based at least in part on the maximum pressure values and the corresponding first timestamps;

determining, based on the determined one or more vital signs, that an alert condition is met, the alert condition comprising a vital sign value being greater than or equal to a predefined threshold vital sign value;

providing, based on the determination that the alert condition is met, an alert indicating that the alert condition has been met; and displaying the one or more vital signs to the user via the display, wherein the one or more vital signs include a heart rate of the user, a heart rate variation of the user, and a respiration rate of the user.

17. The non-transitory computer program product of claim 16, wherein determining the heart rate includes generating a plurality of peak rates by at least subtracting, for each of the plurality of groups of related points, the corresponding first timestamp of the maximum pressure value of a group of related points from the corresponding first timestamp of the maximum pressure value of an immediately subsequent group of related points.

18. The non-transitory computer program product of claim 17, wherein determining the heart rate variation includes:

determining a maximum rate from the plurality of peak rates;

determining a minimum rate from the plurality of peak rates; and determining a standard deviation from the plurality of peak rates.

19. The non-transitory computer program product of claim 16, wherein determining the respiration rate includes:

determining a fundamental frequency of the arterial pulse pressure waveform.

\* \* \* \* \*